(12) United States Patent
Schiemenz et al.

(10) Patent No.: US 6,407,029 B1
(45) Date of Patent: Jun. 18, 2002

(54) MIXTURES COMPRISING TETRAKIS (PYRROLIDINO/PIPERDINO) PHOSPHONIUM SALTS

(75) Inventors: Berthold Schiemenz; Thomas Wessel, both of Frankfurt am Main; Ralf Pfirmann, Griesheim; Andreas Beck, Westerngrund; Walter Hahn, Frankfurt am Main, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/617,470

(22) Filed: Jul. 17, 2000

(30) Foreign Application Priority Data

Jul. 23, 1999 (DE) .......................... 199 34 594

(51) Int. Cl.[7] .................. B01J 27/14; C07D 239/02; C07D 211/72; C07C 45/90; C07C 22/00
(52) U.S. Cl. .................. 502/208; 594/334; 594/409; 546/345; 558/424; 568/433; 568/437; 570/147
(58) Field of Search .................. 570/147; 502/208; 568/433, 431; 558/424; 544/334, 409; 546/345

(56) References Cited

FOREIGN PATENT DOCUMENTS

| WO | WO 97/32832 | 9/1994 |
|---|---|---|
| WO | WO 98/22413 | 5/1998 |
| WO | WO 98/32532 | 7/1998 |
| WO | WO 99/26950 | 6/1999 |

OTHER PUBLICATIONS

J. Gen. Chem, USSR, 52, 1982, pp. 1779–1787.
Derwent Patent Family Abstract for WO 98/32532.
EPO Search Report.
Derwent Patent Family Abstract for WO 97/32832.
J. Gen. Chem, USSR, 52, "Some Properties of Phosphorimdeic Triamides", Feb. 20, 1983, pp. 1779–1787, XP–002065181.

Primary Examiner—Alan L. Rotman
Assistant Examiner—Raymond Covington
(74) Attorney, Agent, or Firm—Scott E. Hanf

(57) ABSTRACT

The present invention relates to mixtures comprising from 70 to 99.5% by weight of a compound of the formula $(R)_4P^+X^-$ (1) and from 30 to 0.5% by weight of a compound of the formula $(R)_3P=O$ (2), where R is in each case a radical

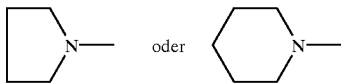

and $X^-$ is an inorganic or organic anion or the equivalent of a multiply charged inorganic or organic anion, also to a process for preparing the mixtures by reacting a phosphorus pentahalide with pyrrolidine or piperidine in the molar ratio 1:6 to 1:50 in the presence of an inert solvent initially at −20 to 80° C., subsequently continuing the reaction at 90 to 180° C., treating the resulting reaction product at 0 to 80° C. with aqueous alkali at a pH of 7 to 15, and separating aqueous and organic phase from one another, and to the use of the mixtures as catalyst and cocatalyst for phase-transfer reactions, nucleophilic substitution reactions or halogen-fluorine exchange reactions.

11 Claims, No Drawings

MIXTURES COMPRISING TETRAKIS (PYRROLIDINO/PIPERDINO) PHOSPHONIUM SALTS

BACKGROUND OF THE INVENTION

The invention relates to mixtures comprising aminophosphonium salts (mixtures of substances), and to the preparation and use thereof.

Aminophosphonium compounds are used, as is evident from WO 98/32532 and WO 98/22413, as catalysts in the preparation of fluorine-containing compounds by a halogen-fluorine exchange reaction (halex reaction). Although the tetrakis(diethylamino)phosphonium bromide used in WO 98/32532 and WO 98/22413 gives good results, it has a very high dermal toxicity. The very high dermal toxicity of <50 mg/kg body weight stands in the way of industrial use, however.

SUMMARY OF THE INVENTION

The object is to provide novel mixtures which comprise high proportions of tetrakisaminophosphonium salts and which are suitable as catalysts or constituent of catalyst systems for phase-transfer reactions, in particular for halogen-fluorine exchange reactions, have a lower dermal toxicity and reach or even exceed the results which can be achieved on use of tetrakis(diethylamino)phosphonium bromide. It is additionally intended that preparation of these mixtures even in industrial quantities be possible in a comparatively simple manner at reasonable expense.

DESCRIPTION OF THE PREFERRED EMBODIMENTS

This object is surprisingly achieved by mixtures comprising from 70 to 99.5% by weight of a compound of the formula $(R)_4P^+X^-$ (1) and from 30 to 0.5% by weight of a compound of the formula $(R)_3P=O$ (2), where R is in each case a radical

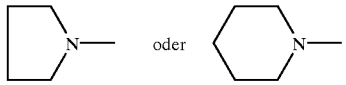

and $X^-$ is an inorganic or organic anion or the equivalent of a multiply charged inorganic or organic anion.

The mixtures comprise high proportions of the compounds of the formula $(R)_4P^+X^-$ (1), namely the appropriate tetrakis(pyrrolidino)phosphonium salts or the tetrakis (piperidino)phosphonium salts. The compounds $(R)_3P=O$ present in the mixture surprisingly have no adverse effects on the catalytic activity so that the mixtures can be employed directly as catalyst or catalyst component.

The dermal toxicity both for tetrakis(pyrrolidino) phosphonium chloride and for tetrakis(piperidino) phosphonium chloride is unexpectedly significantly less than that of tetrakis(diethylamino)phosphonium bromide, although there are no pronounced differences in relation to the molecular structure/molecular size and molecular mass of the tetrakisphosphonium cation. The dermal toxicity of tetrakis(piperidino)phosphonium chloride is ~200 mg/kg body weight, that of tetrakis(pyrrolidino)phosphonium chloride is ~390 mg/kg body weight, and is thus considerably less than that of tetrakis(diethylamino)phosphonium bromide. The data for the dermal toxicities of tetrakis (diethylamino)phosphonium bromide, tetrakis(piperidino) phosphonium chloride and tetrakis(pyrrolidino) phosphonium chloride are derived from our own measurements.

The present invention relates in particular to mixtures comprising 75 to 99, preferably 80 to 98, particularly preferably 85 to 95, % by weight of the compound $(R)_4P^+X^-$ (1) and 25 to 1, preferably 20 to 2, particularly preferably 15 to 5, % by weight of the compound $(R)_3P=O$ (2). R is—as already stated previously—both in the compounds (1) and in the compounds (2) a pyrrolidino or piperidino radical, in particular a pyrrolidino radical.

$X^-$ in the compounds of the formula (1) is $F^-$, $Cl^{31}$, $Br^-$, $I^-$, $ClO_4^-$, $BF_4^-$, $PF_6^-$, $NO_3^-$, $HSO_4^-$, ½ $SO_4^{2-}$, $H_2PO_4^-$, ½ $HPO_4^{2-}$, ⅓ $PO_4^{3-}$, $R''—COO$, where $R''$ is an alkyl radical having 1 to 9 carbon atoms, a phenyl radical, benzyl radical or naphthyl radical, $R'''—SO_3^-$, where $R'''$ is an alkyl radical having 1 to 18 carbon atoms, a phenyl radical, tolyl radical or naphthyl radical, $HCO_3^-$, ½ $CO_3^{2-}$ or ½ $C_6H_4(COO^-)_2$. $X^-$ is, in particular, $F^-$, $Cl^-$, $Br^-$, $I^-$, $BF_4^-$, $PF_6^-$ or ½ $SO_4^{2-}$, preferably $F^-$, $Cl^-$ or $Br^-$, particularly preferably $Cl^-$.

The mixtures normally result as mixtures of substances consisting of 95 to 100, in particular 96 to 99.5, preferably 97 to 99, % by weight of the mixture comprising the compounds $(R)_4P^+X^-$ and $(R)_3P=O$ and 5 to 0, in particular 5 to 0.5, preferably 3 to 1, % by weight of volatile constituents. Volatile constituents which may still be present are, for example, residues of unreacted starting materials and solvents. However, it is possible to remove the volatile constituents very substantially or completely.

G. N. Koidan et al., describe in J. Gen. Chem. USSR (Engl. Transl.) 52, 1982, pages 1779 to 1787, a multistage preparation of tetrakis(piperidino)phosphonium bromide. This entails initial reaction of a compound of the formula $(R_2N)_3P^{+HalHal-}$ with ammonia, and preparation from the reaction product which is formed, with elimination of water, of a triamide of an iminophosphoric acid (phosphorimidic triamide).

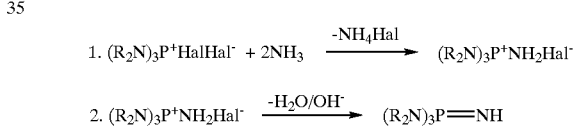

The triamide of the iminophosphoric acid is then converted with 1,5-dibromopentane in accordance with the following reaction equations $(R_2N)_3P=NH+Br(CH_2)_5Br \rightarrow (R_2N)_3P=N—(CH_2)_5—Br$  3.

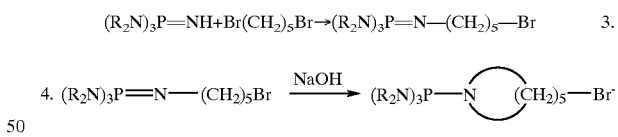

by a ring-closure reaction into tetrakis(piperidino) phosphonium bromide.

This type of synthesis is very complicated, requires several reaction stages and leads to a reaction product which, besides the tetrakis(piperidino)phosphonium bromide, still contains strongly basic compounds of the formula $(R_2N)_3P=NH$ and $(R_2N)_3P=N—(CH_2)_5Br$. These compounds interfere with the catalytic activity, in particular with the selectivity for particular halex reactions.

There is consequently a need to provide a process for preparing tetrakis(piperidino)phosphonium salts which avoids the aforementioned disadvantages, can be implemented even industrially in a straightforward manner and makes the required products available in good yields.

The object is achieved by a process for preparing the aforementioned mixtures comprising the compounds $(R)_4P^+$ $X^-$ and $(R)_3P{=}O$. It comprises reacting a phosphorus pentahalide with pyrrolidine or piperidine in the molar ratio 1:6 to 1:50 in the presence of an inert solvent, initially at 10 to 80° C., subsequently continuing the reaction at 90 to 180° C., treating the resulting reaction product at 0 to 80° C. with aqueous alkali at a pH of 7 to 15, and separating aqueous and organic phase from one another.

Normally pyrrolidine or piperidine is added to the mixture of phosphorus pentahalide and solvent, but the reverse procedure is also possible. The reaction moreover proceeds initially in the aforementioned temperature range. The temperature should ordinarily be kept in the stated temperature range, where appropriate by cooling. Care must be taken that the reactants are thoroughly mixed. This reaction step is particularly straightforward when pyrrolidine or piperidine is added at a rate such that said temperature range is maintained.

Following this reaction step the reaction is, as stated above, continued at a higher temperature, at which the required tetrakis(pyrrolidino)- or tetrakis-(piperidino) phosphonium salt is formed.

Long reaction times and high reaction temperatures favor the formation of the tetrakis(pyrrolidino)- or tetrakis (piperidino)phosphonium salts, whereas shorter reaction times and low reaction temperatures lead to mixtures with an increased proportion of $(R)_3P{=}O$ compounds.

After completion of this reaction, the reaction product is, as already mentioned above, treated at a temperature of from 0 to 80° C. with an aqueous alkali. The amount of alkali employed is such that a pH of 7 to 15 is maintained during the treatment. The treatment with the aqueous alkali leads to hydrolysis of hydrolyzable constituents of the reaction product. The compounds of the formula $(R)_3P{=}O$ (2) presumably result from this hydrolysis and may be produced in varying amounts. A further effect of the treatment with aqueous alkali is that the hydrohalides of pyrrolidine or piperidine which are formed during the reaction are neutralized, and pyrrolidine or piperidine is liberated. The liberated pyrrolidine or piperidine can be recovered and reused in the reaction.

The aqueous phase is separated from the organic phase which contains the required reaction product, solvent, and excess pyrrolidine or piperidine used and/or that liberated from the hydrohalides. The organic phase is then concentrated, for example by vacuum distillation, to dryness. The solid produced thereby contains the mixtures according to the invention and can be employed directly, for example as catalyst or catalyst constituent.

In the light of the prior art described in J. Gen. Chem. USSR (Engl. Transl.) 52, 1982, pages 1779 to 1787, it may be regarded as surprising that the tetrakis(piperidino) phosphonium salts can be prepared directly by reacting a phosphorus pentahalide with piperidine.

In view of the severe reaction conditions used in the preparation according to the invention, in particular the high temperatures, it is not to be expected that it is possible to prepare a mixture comprising essentially only two compounds with a high proportion of tetrakis(pyrrolidino)- or tetrakis(piperidino)phosphonium salts and employable directly as catalyst or catalyst constituent.

Reactions taking place at high temperatures normally lead to reaction products consisting of a large number of different reaction products and having impurities preventing use as catalyst—without the need to undertake elaborate additional purification. Catalyst poisons act, as the skilled worker knows, even in very small quantities. The mixtures contain no interfering $(R)_3P{=}NR'$ (R'=hydrogen, alkyl, alkenyl having 1 to 6 carbon atoms or —$(CH_2)_x$Hal, where x=2 to 5 and Hal is Cl or Br). Compounds of this type are known to be strong bases (see, for example: R. Schwesinger et. al., Chem. Ber.1994, 127, 2435–2454, in particular page 2440 herein).

In a large number of cases, the phosphorus pentahalide is reacted with pyrrolidine or piperidine in the molar ratio 1:7 to 1:25, in particular 1:8 to 1:16, preferably 1:8 to 1:14. Phosphorus pentahalide is reacted with pyrrolidine or piperidine, as mentioned at the outset, initially at −20 to 80, in particular 20 to 75, preferably 40 to 70° C.

The inert solvent employed is an aliphatic, cycloaliphatic or aromatic hydrocarbon or a mono- or polychlorinated aliphatic, cycloaliphatic or aromatic hydrocarbon.

Examples of very suitable inert solvents are hexane, cyclohexane, methylcyclohexane, toluene, ethylbenzene, mesitylene, o-xylene, m-xylene, p-xylene, technical mixtures of isomeric xylenes, methylene chloride, tetrachloroethane, chlorobenzene, dichlorobenzene or chlorotoluene, in particular o-xylene, m-xylene, p-xylene, technical mixtures of isomeric xylenes, chlorobenzene. Mixtures of solvents can also be used.

Use of excess pyrrolidine or piperidine as solvent is likewise suitable. In this case, phosphorus pentahalide suspended or dissolved in an inert solvent, but not in pyrrolidine or piperidine, is metered in to pyrrolidine or piperidine, with mixing.

The reaction is continued, as already mentioned above, at 90 to 180, preferably 100 to 170, preferably 120 to 150° C.

It is particularly simple to continue the reaction under reflux conditions, choosing a solvent which has a boiling point within the aforementioned temperature ranges.

However, it is also possible to carry out the reaction under pressure. It is thus also possible, if required, to employ solvents with lower boiling points.

In a particular variant, phosphorus pentachloride or phosphorus pentabromide, in particular phosphorus pentachloride, is employed as phosphorus pentahalide. It is also possible to prepare the phosphorus pentahalide in a preceding reaction step from the corresponding phosphorus trihalide and the halogen.

After completion of the reaction, the reaction product is treated, as already mentioned, at 0 to 100, in particular 10 to 70, preferably 25 to 50° C. with aqueous alkali at a pH of 7 to 15, in particular 8 to 14.5, preferably 9 to 14. An example of a suitable aqueous alkali is a 5 to 50, in particular 15 to 30, preferably 15 to 25, % by weight of aqueous alkali metal or alkaline earth metal hydroxide solution. It is particularly simple to use a corresponding aqueous NaOH or KOH, in particular an NaOH, solution. It has proven suitable in many cases to use a 20 to 25% strength aqueous NaOH or KOH, in particular NaOH.

Care must be taken that mixing is thorough during the treatment of the reaction product with the alkali.

Following the treatment of the reaction product with the alkali, the aqueous phase is separated from the organic phase. The mixtures comprising the compound $(R)_4P^+X^-$ and $(R)_3P{=}O$ are present in the organic phase. Removal of volatile constituents, which include the solvent and pyrrolidine or piperidine still present, results in the mixtures as solid. If required, it is possible to increase the proportion of tetrakis(pyrrolidino)phosphonium salts or tetrakis (piperidino)phosphonium salts by recrystallization. The $X^-=Cl^-$ or $Br^-$ can be exchanged for other of the above mentioned anions by salt metathesis, if desired.

The invention further relates to the use of the mixtures described above in detail which comprise the compound of the formula $(R)_4P^+X^-$ (1) and the compound of the formula $(R)_3P{=}O$ (2), in which R and $X^-$ have the aforementioned meaning, as catalyst or cocatalyst for phase-transfer reactions, nucleophilic substitution reactions or halogen-fluorine exchange reactions, in particular for phase-transfer reactions or halogen-fluorine exchange reactions, preferably for halogen-fluorine exchange reactions.

Suitable as catalyst for halogen-fluorine exchange reactions (halex reactions) are, for example, mixtures of substances comprising one of the mixtures described above which comprise the compound of the formula $(R)_4P^+X^-$ (1) and the compound of the formula $(R)_3P=O$ (2), in which R and $X^-$ have the aforementioned meaning, and at least one compound selected from the group of quaternary ammonium compounds of the formula

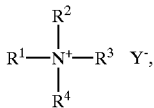
(3)

quaternary ammonium salts or phosphonium salts of the formula

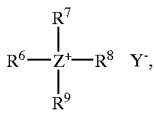
(4)

polyethers of the formula $R^{10}-(O-C_xH_{2x})_s-OR^{11}$ (5) and crown ethers, in which in formula (3), $R^1$, $R^2$ and $R^3$ are identical or different and are a linear or branched radical of the formula $-(C_pH_{2p}O)_rR^5$ in which $R^5$ is hydrogen or a linear or branched alkyl radical having 1 to 16 carbon atoms, p is an integer from 1 to 10 and r is an integer from 1 to 15;

or a linear or branched alkyl radical having 1 to 30 carbon atoms;

or an unsubstituted phenyl or naphthyl radical, or a substituted phenyl or naphthyl radical, where the substituents have the meaning of halogen, $C_1$–$C_4$-alkyl, $C_1$–$C_4$-alkoxy, nitro or cyano;

$R^4$ is a linear or branched radical of the formula $-(C_pH_{2p}O)_rR^5$; and $Y^-$ is an inorganic anion;

and in formula (4)

$R^6$, $R^7$, $R^8$ and $R^9$ are identical or different and are a linear or branched alkyl radical having 1 to 22 carbon atoms; or an unsubstituted or substituted aryl radical or a $C_1$–$C_4$-alkylaryl radical, where aryl has the meaning of phenyl or naphthyl, and said substituents are halogen, $C_1$–$C_4$-alkyl, $C_1$–$C_4$-alkoxy, nitro or cyano; Z has the meaning of N or P, and $Y^-$ is an inorganic anion;

and in formula (5)

$R^{10}$ and $R^{11}$ are identical or different and are a linear or branched alkyl radical having 1 to 16 carbon atoms;

x is an integer from 2 to 6 and s is an integer from 1 to 60;

or one of the radicals $R^{10}$ and $R^{11}$ is hydrogen and the other of the radicals is a linear or branched alkyl radical having 1 to 16 carbon atoms, x is an integer from 2 to 6 and s is an integer from 2 to 50, or the radicals $R^{10}$ and $R^{11}$ are hydrogen, x is an integer from 2 to 6 and s is an integer from 3 to 5.

Suitable catalysts for halogen-fluorine exchange reactions are mixtures of substances comprising one of the mixtures described above comprising the compound $(R)_4P^+X^-$ and the compound $(R)_3P=O$, and at least one compound selected from a group of quaternary ammonium compounds of the formula (3), quaternary ammonium salts and phosphonium salts of the formula (4), polyethers of the formula (5) and crown ethers, in which in formula (3), $R^1$, $R^2$ and $R^3$ are identical or different and are a linear or branched radical of the formula $-(C_pH_{2p}O)_rR^5$ in which $R^5$ is hydrogen or a linear or branched alkyl radical having 1 to 8 carbon atoms, p is an integer from 1 to 5 and r is an integer from 2 to 10; or a linear or branched alkyl radical having 1 to 18 carbon atoms; or an unsubstituted phenyl or naphthyl radical; $R^4$ is a linear or branched radical of the formula $-(C_pH_{2p}O)_rR^5$, in which $R^5$ is hydrogen or a linear or branched alkyl radical having 1 to 8 carbon atoms, p is an integer from 1 to 5 and r is an integer from 2 to 10. Particularly of interest as catalyst for halogen-fluorine exchange reactions are mixtures of substances which comprise one of the mixtures described above and at least one compound from the group of quaternary ammonium compounds of the formula (3).

The mixtures of substances normally comprise 5 to 95% by weight, in particular 20 to 80% by weight, preferably 25 to 75% by weight, of a mixture comprising the compound $(R)_4P^+X^-$ and $(R)_3P=O$. The residual 95 to 5% by weight, in particular 80 to 20% by weight, preferably 75 to 25% by weight, of the mixtures of substances are accounted for by the remainder, namely at least one compound selected from the group of quaternary ammonium compounds of the formula (3), of quaternary ammonium or phosphonium salts of the formula (4), polyethers of the formula (5) and crown ethers, in particular at least one compound from the group of quaternary ammonium compounds of the formula (3).

EXAMPLES

The following examples describe the invention further without restricting it.
Experimental Section Example 1

Preparation of a Mixture A Comprising Tetrakis (pyrrolidino)phosphonium Chloride and Tris (pyrrolidino)phosphine Oxide 104.12 g (0.5 mol) of phosphorus pentachloride are dissolved in 700 g of dry xylene at 50° C. Then 426.7 g (6 mol) of pyrrolidine are added dropwise in such a way that the internal temperature does not exceed 75° C. After the addition, the mixture is heated to reflux for 15 hours. It is then cooled to 40° C. and hydrolyzed with 800 g (4 mol) of 20% strength aqueous sodium hydroxide solution. After removal of the aqueous phase, the organic phase is evaporated to dryness in a rotary evaporator. Pyrrolidine is redistilled out of the distillate and reused. 172.8 g of a pale brownish solid are obtained, consisting of 94% tetrakis (pyrrolidino)phosphonium chloride, 5% tris(pyrrolidino) phosphine oxide and 1% unidentified constituents (mixture A). The product obtained in this way is used directly as catalyst and cocatalyst for halex reactions (see also Examples 3 and 4).

Elemental analysis: C=55.4%, H=9.3%, Cl=9.8%, N=16.1%, O=0.3%, P=9.0%

To isolate the pure components, this crude mixture is boiled in tetrahydrofuran (THF) and, after filtration, 161 g (93% of theory) of tetrakis(pyrrolidino)phosphonium chloride are isolated as a colorless powder. Tris(pyrrolidino) phosphonium oxide is isolated from the THF phase by kugelrohr distillation. Mixtures of any composition can be prepared by mixing the pure components.

Tetrakis(pyrrolidino)phosphonium chloride pure: $^1$H-NMR: δ=3.19 (m, 16H, NC$\underline{H}_2$), 1.87 (m, 16H, NCH$_2$C$\underline{H}_2$); $^{13}$C-NMR: δ=46.43 (2 C, J$_P$, c [Hz]=4.8, N$\underline{C}$H$_2$), 25.64 (2C, J$_P$, c [Hz]=8.3, NCH$_2\underline{C}$H$_2$), $^{31}$P-NMR: δ=26.0 (s, 1P).

Example 2

Preparation of a Mixture B Comprising Tetrakis (piperidino)phosphonium Chloride and Tris (piperidino)phosphine Oxide Tetrakis(piperidino)phosphonium chloride is prepared in analogy to Example 1 from 104.12 g (0.5 mol) of phosphorus pentachloride in 730 g of chlorobenzene as solvent and 510.9 g (6 mol) of piperidine.

197.8 g of a pale brownish powder are obtained, consisting of 92% tetrakis(piperidino)phosphonium chloride, 7% tris(piperidino)phophine oxide and 1% nonidentified constituents (mixture B). The product obtained in this way is used directly as catalyst and cocatalyst for halex reactions (see also Examples 3 and 4).

Elemental analysis: C=67.54%, H=11.63%, Cl=9.84%, N=16.16%, O=0.23%, P=9.04%

The pure components are isolated in analogy to Example 1.

Tetrakis(piperidino)phosphonium chloride pure:
$^1$H-NMR: δ=3.14 (m, 16H, NC$\underline{H}_2$), 1.71 (m, 8H, NCH$_2$CH$_2$C$\underline{H}_2$), 1.64 (m, 16H, NCH$_2$C$\underline{H}_2$); $^{13}$C-NMR: δ=47.0 (2 C, N$\underline{C}$H$_2$), 25.73 (2 C, NCH$_2$$\underline{C}$H$_2$), 23.61 (2 C, NCH$_2$CH$_2$$\underline{C}$H$_2$), $^{31}$P-NMR: δ=38.8 (s, 1P).

Comparative Example A

Preparation of Tetrakis(diethylamino)phosphonium Bromide (Comparison Substance)

109.7 g (1.5 mol) of diethylamine are added dropwise to 52.1 g (0.25 mol) of PCl$_5$ in 220 ml of chlorobenzene in 1 hour so that the internal temperature does not exceed 10° C. After the addition, the mixture is stirred at 30° C. for 1 hour and then, at T=15° C., 30 g of ammonia are passed in. After 1 hour, 340 g of 20% strength aqueous sodium hydroxide solution are added, and the aqueous phase is separated off. The excess diethylamine is distilled out of the organic phase. Then 170 g of 50% strength sodium hydroxide solution and 60 g (0.55 mol) of ethyl bromide are added, and the mixture is heated at 50° C. for 4 hours. After phase separation, the organic phase is acidified to pH 6 to 7 with 60% strength hydrobromic acid. Removal of all the volatile constituents by distillation results in 83.9 g tetrakis(diethylamino) phosphonium bromide as a pale brownish oil. 1.5% by weight of the imino-tris(dialkylamino)phosphorane (Et$_2$N)$_3$P=NEt are obtained as impurity. The product obtained in this way (comparison substance) is used directly as catalyst and cocatalyst for halex reactions (see also Examples 3 and 4).

Comparative Example B

Attempt to React PCl$_5$ and Diethylamine to Give Tetrakis(diethylamino)phosphonium Chloride 73.1 g (1.0 mol) of diethylamine are added dropwise at T<15° C. to 20.8 g (0.1 mol) of PCl$_5$ in 180 ml of xylene. After the addition, the mixture is heated to reflux for 2 hours. Cooling to 22° C. is followed by hydrolysis with 160 g of 25% strength aqueous sodium hydroxide solution. The hydrolysis is highly exothermic (temperature rise to 48° C.). The aqueous phase is separated off, and the remaining organic phase is concentrated in a rotary evaporator. Kugelrohr distillation results in 24.9 g of tris(diethylamino) phosphine oxide as a yellow oil. No formation of tetrakis (diethylamino)phosphonium chloride is observed.

Comparative Example C

Preparation of Tetrakis(piperidino)phosphonium Bromide

To 41.65 g (0,2 mol) of phosphorous pentachloride in 220 g chlorobenzene 102.18 g (1,2 mol) of piperidine is added at 5° C. After stirring for 30 min 40 g of ammonia is blown into the suspension at 10° C. After 30 min. the suspension is hydrolyzed at 40° C. with 130 g of caustic soda (50% aqueous solution). After separation of the water phase volatile compounds are evaporated from the organic phase at 120° C./10 mbar. The residue is distilled at 0,1 mbar over a short distillation column to yield 37 g (0.124 mol) of pure tris(piperidino)phosphorous imine (Pip)$_3$P=NH (Mw.: 298.41). 14.92 g (0.05 mol) of the received tris(piperidino) phosphorous imine are dissolved in 100 ml of caustic soda, 40% by weight in water. 12.65 g (0.055 mol) of 1,5-dibrompentane is added dropwise in 20 min. After stirring for two hours at ambient temperature the reaction mixture is heated to 1 00° C. After cooling to 20° C. the mixture is extracted with three portions of methylene chloride (3×20 ml). After drying over sodium sulfate volatile compounds are evaporated from the organic extracts via rotary evaporator. 21.4 g (0.48 mol) of tetrakis(piperidino)phosphonium bromide are obtained.

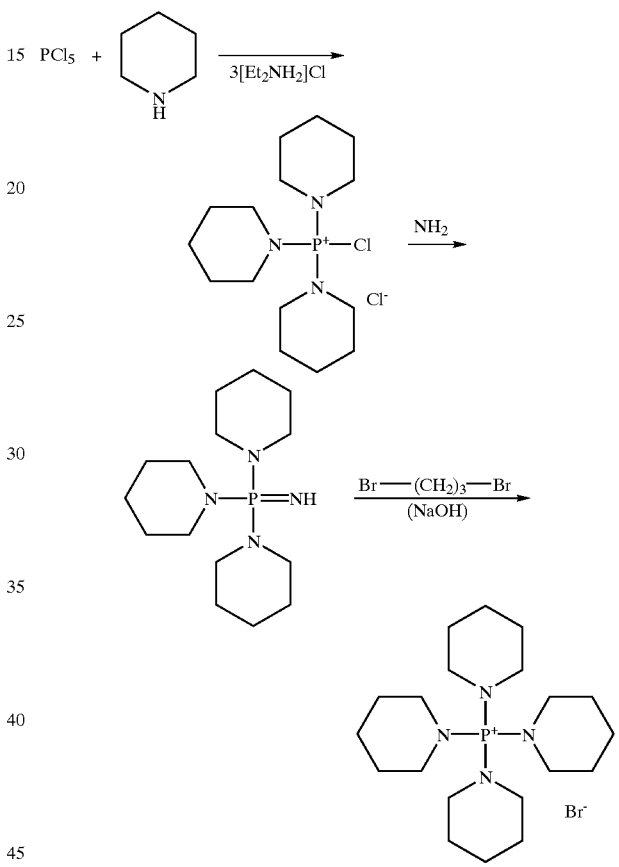

Example 3

Synthesis of 4-fluorobenzaldehyde

At 60° C., a solution of 12.0 g (0.03 mol) of tetrakis (diethylamino)phosphonium bromide in 12 g of N-methylpyrrolidone (NMP), 174.3 g (3 mol) of potassium fluoride, 4.1 g (0.03 mol) of nitrotoluene and 18 ml of xylene are successively added to 421.7 g (3 mol) of 4-chlorobenzaldehyde (4-CBAL). The reaction mixture is dried by azeotropic distillation of the xylene under reduced pressure. After 24 hours at 1 90° C., the formation of 4-fluorobenzaldehyde (4-FBAL) and of benzaldehyde produced by dehalogenation, and the conversion of the reaction are determined by gas chromatography.

In the examples according to the invention, in place of tetrakis(diethylamino)phosphonium bromide an equivalent molar quantity (in each case 0.03 mol) of the aminophosphonium salt indicated in each case in the form of mixture A and B (prepared as in Example 1 and 2) is employed. The procedure is otherwise analogous. The data in Table 1 correspond to GC percentage areas. The difference from 100% indicated in Table 1 as remainder is a measure of side reactions and decomposition.

TABLE 1

Yields of 4-fluorobenzaldehyde (4-FBAL) from the halex reaction of 4-chlorobenzaldehyde (4-CBAL) in GC % areas

| Aminophosphonium salt | 4-FBAL | 4-CBAL | Benzaldehyde | Remainder |
|---|---|---|---|---|
| [(Et$_2$N)$_4$P]Br* | 47.8 | 34.5 | 0.23 | 17.5 |
| [(Pyrrolidino)$_4$P]Cl** | 56.7 | 29.6 | 0.03 | 14.1 |
| [(Piperidino)$_4$P]Cl*** | 54.2 | 32.5 | 0.02 | 13.3 |
| [(Piperidino)$_4$P]Br**** | 42.9 | 38.9 | | 18.2 |

*Comparative example using the comparison substance obtained from Comparative Example A
**Example according to the invention using mixture A obtained from Example 1
***Example according to the invention using mixture B obtained from Example 2
****Comparative example using the comparison substance obtained from Comparative Example C

Example 4

Synthesis of 2-chloro-6-fluorobenzaldehyde and 2,6-difluorobenzaldehyde

At 60° C., 8.8 g (0.02 mol) of tetrakis(diethylamino)phosphonium bromide, 35.2 g (0.06 mol) of methyltris(methyltetraethoxy)ammonium chloride [{CH$_3$(O—C$_2$H$_4$)$_4$}$_3$NCH$_3$]Cl, 72.6 g (1.25 mol) of potassium fluoride and 10 xylene are successively added to 175.0 g (1 mol) of 2,6-dichlorobenzaldehyde (DCBAL). The reaction mixture is dried by azeotropic distillation of the xylene under reduced pressure. After 20 hours at 165° C., the formation of 2-chloro-6-fluorobenzaldehyde (CFBAL), 2,6-difluorobenzaldehyde (DFBAL) and o-chlorobenzaldehyde (o-CBAL) produced by dehalogenation, and the conversion of the reaction are determined by gas chromatography.

In the examples according to the invention, in place of tetrakis(diethylamino)phosphonium bromide an equivalent molar quantity (in each case 0.02 mol) of the aminophosphonium salt indicated in each case in the form of mixture A and B (prepared as in Example 1 and 2) is employed. The procedure is otherwise analogous. The data in Table 2 correspond to GC percentage areas. The difference from 100% indicated in Table 2 as remainder is a measure of side reactions and decomposition.

TABLE 2

Yields of 2,6-difluorobenzaldehyde (DFBAL) and 2-chloro-6-fluorobenzaldehyde (CFBAL) from the halex reaction of 2,6-dichlorobenzaldehyde (DCBAL) in GC % areas

| Aminophosphonium salt | DFBAL | CFBAL | DCBAL | o-CBAL | Remainder |
|---|---|---|---|---|---|
| [(Et$_2$N)$_4$P]Br* | 32.1 | 37.0 | 10.1 | 0.81 | 20.0 |
| [(Pyrrolidino)$_4$P]Cl** | 33.6 | 42.0 | 5.4 | 0.24 | 18.7 |
| [(Piperidino)$_4$P]Cl*** | 33.3 | 44.4 | 4.9 | 0.19 | 17.2 |
| [(Piperidino)$_4$P]Br**** | 19.4 | 41.4 | 19.8 | 0.52 | 18.9 |

*Comparative example using the comparison substance obtained from Comparative Example A
**Example according to the invention using mixture A obtained from Example 1
***Example according to the invention using mixture B obtained from Example 2
****Comparative example using the comparison substance obtained from Comparative Example C

What is claimed is:

1. A mixture comprising from 70 to 99.5% by weight of a compound of the formula (R)$_4$P$^+$X$^-$ (1) and from 30 to 0.5% by weight of a compound of the formula (R)$_3$P=O (2), where R is in each case a radical

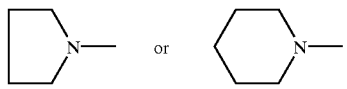

and X$^-$ is an inorganic or organic anion or the equivalent of a multiply charged inorganic anion.

2. A mixture comprising from 75 to 99% by weight of the compound (R)$_4$P$^+$X$^{51}$ and from 25 to 1% by weight of the compound (R)$_3$P=O.

3. A mixture comprising from 80 to 98% by weight of the compound (R)$_4$P$^+$X$^-$ and from 20 to 2% by weight of the compound (R)$_3$P=O.

4. A mixture as claimed in claim 1, wherein X$^-$ is F$^-$, Cl$^-$, Br$^-$, I$^-$, ClO$_4^-$, BF$_4^-$, PF$_6^-$, NO$_3^-$, HSO$_4^-$, ½ SO$_4^{2-}$, H$_2$PO$_4^-$, ⅓ PO$_4^{3-}$, R"COO$^-$, where R" is an alkyl radical having 1 to 9 carbon atoms, a phenyl radical, benzyl radical or naphthyl radical, R'"—SO$_3^-$, where R'" is an alkyl radical having 1 to 18 carbon atoms, a phenyl radical, a tolyl radical or a naphthyl radical, HCO$_3^-$, ½ CO$_3^{2-}$ or ½ C$_6$H$_4$(COO$^-$)$_2$.

5. A process for preparing mixtures as claimed in claim 1, which comprises reacting a phosphorus pentahalide with pyrrolidine or piperidine in the molar ratio 1:6 to 1:50 in the presence of an inert solvent initially at −20 to 80° C., subsequently continuing the reaction at 90 to 180° C., treating the resulting reaction product at 0 to 80° C. with aqueous alkali at a pH of 7 to 15, and separating aqueous and organic phase from one another.

6. The process as claimed in claim 5, wherein the phosphorus pentahalide is reacted with pyrrolidine or piperidine in the molar ratio 1:8 to 1:25.

7. The process as claimed in claim 5, wherein an aliphatic, cycloaliphatic or aromatic hydrocarbon or a mono- or polychlorinated aliphatic, cycloaliphatic or aromatic hydrocarbon is employed as inert solvent.

8. The process as claimed in claim 5, wherein the phosphorus pentahalide is reacted with pyrrolidine or piperidine initially at 20 to 75° C.

9. The process as claimed in claim 5, wherein the reaction is continued at 100 to 170° C.

10. The process as claimed in claim 5, wherein phosphorus pentachloride is employed as phosphorus pentahalide.

11. A method for performing phase transfer reactions, nucleophilic substitution reactions or halogen-fluorine exchange reactions which include the steps of:

provm the mixtures as claimed in claim 1 as a catalyst and a cocatalyst;

providing reactants; and reacting reactants in the presence of said mixtures as a catalyst and a cocatalyst.

* * * * *